US012653639B2

(12) United States Patent
Foroughi et al.

(10) Patent No.: US 12,653,639 B2
(45) Date of Patent: Jun. 16, 2026

(54) MULTI-MODAL FIDUCIAL MARKER

(71) Applicant: Clear Guide Medical, Inc., Baltimore, MD (US)

(72) Inventors: Pezhman Foroughi, Baltimore, MD (US); Alican Demir, Baltimore, MD (US)

( * ) Notice: Subject to any disclaimer, the term of this patent is extended or adjusted under 35 U.S.C. 154(b) by 0 days.

(21) Appl. No.: 18/632,534

(22) Filed: Apr. 11, 2024

(65) Prior Publication Data

US 2024/0261059 A1     Aug. 8, 2024

Related U.S. Application Data

(62) Division of application No. 17/214,892, filed on Mar. 28, 2021, now Pat. No. 12,011,323.

(51) Int. Cl.
A61B 90/00 (2016.01)

(52) U.S. Cl.
CPC ...... A61B 90/39 (2016.02); *A61B 2090/3954* (2016.02); *A61B 2090/3966* (2016.02); *A61B 2090/3995* (2016.02)

(58) Field of Classification Search
CPC .. A61B 90/39; A61B 2090/3904–3995; A61B 8/4281
See application file for complete search history.

(56) References Cited

U.S. PATENT DOCUMENTS 5,368,030 A * 11/1994 Zinreich ................. A61B 90/39
                                                        324/309
5,469,847 A * 11/1995 Zinreich ................... H05G 1/26
                                                        324/309

5,868,673 A * 2/1999 Vesely ...................... G01H 3/00
                                                        600/407
8,620,405 B2 * 12/2013 McClelland ............. A61B 6/12
                                                        378/163
2015/0223906 A1 * 8/2015 O'Neill ................ A61B 6/0492
                                                        600/407
2017/0340039 A1 * 11/2017 Jur ........................ A01K 15/02
2018/0214125 A1 * 8/2018 Tola ..................... A61B 8/4281
2020/0320721 A1 * 10/2020 Holladay .............. A61B 90/39
2021/0127858 A1 * 5/2021 Joines ................... G09B 23/32
2021/0223855 A1 * 7/2021 Gibby .................... G06F 3/011
2021/0338195 A1 * 11/2021 Reiche .................. A61B 90/39
2022/0008141 A1 * 1/2022 Chopra .................. A61B 6/461

OTHER PUBLICATIONS

Andress et al. "On-the-fly augmented reality for orthopedic surgery using a multimodal fiducial," Journal of Medical Imaging 5(2), 021209 (Jan. 26, 2018). https://doi.org/10.1117/1.JMI.5.2.021209. (Year: 2018).*

* cited by examiner

*Primary Examiner* — Anh Yuan T Nguyen
*Assistant Examiner* — Younhee Choi

(57) ABSTRACT

A multi-layer fiducial marker includes a graphic pattern layer having an upper surface and a lower surface, the upper surface including dark pattern disposed on a white background. The lower surface may be coated with a radiopaque material and a hard coat film layer may be disposed over the radiopaque material. A cup is provided having an upper rim, a trough and a lower surface. A ballistic gel layer having upper and lower surfaces is disposed in the trough of the cup. A first adhesive layer is disposed between the ballistic gel layer and the hard coat film layer. A second adhesive layer is affixed to a lower surface of the cup and a skin interface layer is stacked thereunder.

14 Claims, 5 Drawing Sheets

MULTI-MODAL FIDUCIAL MARKER

FIELD OF THE INVENTION

The device of the present application relates to surface markers useful in multiple diagnostic imaging techniques.

BACKGROUND

Radiologists and others use a number of methods to create images of structures within a patient's body to help diagnose diseases and guide therapeutic procedures. Methods used include, for example, conventional X-Ray, Computerized Tomography ("CT"), ultrasound, Positron Emission Tomography ("PET"), and Magnetic Resonance Imaging ("MRI"), among others. These methods respectively employ X-radiation (both the X-Ray and CT methods), sound, radioactive emissions, and magnetic fields in combination with radiofrequency electromagnetic radiation, to create images of structures within the patient's body.

When creating such diagnostic images of a patient, it is desirable to use surface anatomical features which are visible both on the patient and on the diagnostic image of that patient as reference points to facilitate the performance of surgical or other therapeutic intervention techniques. Reference points defined on both a patient's body and a diagnostic image of interior features of that patient's body, allow a physician to geometrically calculate the precise location of a particular site within the patient's body or a particular position of a specific structure within the patient's body. Pin-pointing the location of a particular site or structure allows the physician to more easily and accurately biopsy or otherwise treat the area.

However, there often are no surface anatomical features on the patient's body adequate to use as such reference points (e.g. such features may not exist or may not be located appropriately for such use). If there are no anatomical reference points on the surface of the patient's body, one is unable to precisely locate a target site or structure shown in a two-dimensional diagnostic image. The location of the target site or structure is obscure because the two-dimensional diagnostic image does not provide sufficient information for a geometric relationship between a surface point on the patient's body and the target site or structure to be accurately calculated (i.e. it is unclear at what point on the patient's body the diagnostic image scan was taken).

In such cases, it is desirable to place artificial reference markers on the patient's skin to serve as reference points. A physician may place artificial markers in positions which are optimal reference points relative to the location of target tissues within the patient's body. The markers are designed to clearly show unique and identifiable reference points on both the surface of the patient's body and on the diagnostic image.

Furthermore, it is becoming increasingly important to align images formed by different imaging methods to better identify pathologic structures. Aligning, or "rectifying," images and other radiographic data formed by different imaging methods would be substantially improved (in both ease and accuracy) through the use of surface markers which create reference points visible to a multiplicity of imaging methods. Such surface markers would facilitate the precise super-imposition of imaging data from CT, MRI, and other sources for optimal correlation of tissues and physiologic processes which are demonstrated using these various methods.

Surface markers of various shapes and sizes are generally known in the prior art. However, such prior art surface markers suffer from various limitations. For example, many prior art markers are visible only under select imaging methods. Other prior art markers are not readily distinguishable using standard machine vision techniques.

Therefore, a need remains for improved multi-modal markers that are detectable under diagnostic imaging and that are readily distinguishable using standard machine vision techniques.

SUMMARY OF THE INVENTION

In one embodiment a multi-layer fiducial marker device is provided. The device may include a first layer having an upper surface and a lower surface, the upper surface including a dark pattern disposed on a white background, the lower surface being coated with a radiopaque material and a hard coat film layer disposed over the radiopaque material; a cup having an upper rim, a trough and a lower surface; a ballistic gel layer having an upper surface and a lower surface, the ballistic gel layer being disposed in the trough of said cup; a first adhesive layer contiguous to said graphic pattern layer and the upper surface of said ballistic gel layer and the rim of said cup; and a second adhesive layer affixed to the lower surface of said cup.

In another embodiment a multi-layer fiducial marker device is provided. The device may include a graphic pattern layer having an upper surface and a lower surface, the upper surface including a dark pattern disposed on a white background, the lower surface being coated with a radiopaque material and a hard coat film layer disposed over the radiopaque material; a ballistic gel layer having an upper surface and a lower surface; a first adhesive layer disposed between said graphic pattern layer and the upper surface of said ballistic gel layer; and a second adhesive layer affixed to the lower surface of said ballistic gel assembly.

In still another embodiment a fiducial marker assembly is provided The assembly may include a substrate; a plurality of multilayer fiducial markers, each of said plurality of fiducial markers including a graphic pattern layer having an upper surface and a lower surface, the upper surface including a dark pattern disposed on a white background, the lower surface being coated with a radiopaque material and a hard coat film layer disposed over the radiopaque material; a ballistic gel layer having an upper surface and a lower surface; a first adhesive layer disposed between said graphic pattern layer and the upper surface of said ballistic gel layer; and a second adhesive layer affixed to the lower surface of said ballistic gel assembly; each of said plurality of multilayer fiducial markers being removably attached to said substrate and each of said plurality of multilayer fiducial markers having a unique dark pattern disposed on the upper surface.

In still a further embodiment, a multi-layer fiducial marker device is provided. The device may include a first layer having an upper surface including a dark pattern disposed on a white background, a lower surface and a hard coat film layer disposed over the lower surface; a cup having an upper rim, a trough and a lower surface; a ballistic gel layer having an upper surface and a lower surface, the ballistic gel layer being disposed in the trough of said cup; a first adhesive layer contiguous to said graphic pattern layer and the upper surface of said ballistic gel layer and the rim of said cup; and a second adhesive layer affixed to the lower surface of said cup.

DETAILED DESCRIPTION

The present disclosure describes embodiments of multi-modal fiducial markers which may be adequately imaged by CT, MRI, X-ray, fluoroscopy, via cameras; and are readily distinguishable by standard machine vision cameras. The markers described herein are suitable for use in image-based navigation systems such as those described in U.S. Pat. No. 9,436,993, U.S. Patent Application Publication No. 2019/0374290 and U.S. Patent Application Publication No. 2019/0374291.

Figure 1:
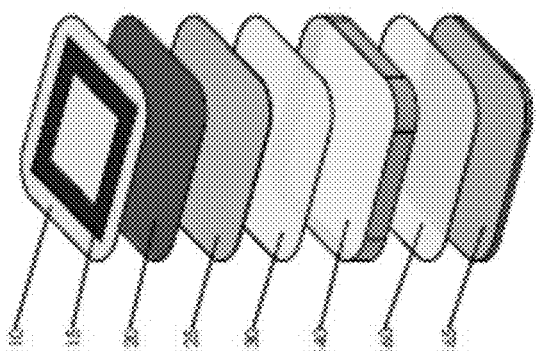
FIG. 1 depicts an exploded view of a multi-modal marker in accordance with an embodiment of the invention.

As illustrated in FIG. 1, in accordance with the present invention, a multi-modal fiducial marker of the present invention 100 comprises a multi layered structure including a graphic pattern or registration layer 110 that allows observing cameras to localize the marker in up to six degrees of freedom in camera coordinates. Graphic pattern layer 110 includes an upper surface and a lower surface. The upper surface of graphic pattern layer 110 includes a surface pattern 115 realized by a dark, e.g., black, pattern disposed on a light, e.g., white, background. In some embodiments the surface pattern includes a plurality of dark squares disposed on a white background. Other pattern geometries may also be employed. In some embodiments, graphic pattern layer 110 may include April tags.

A first imaging modality layer 120 may be disposed adjacent to and stacked underneath graphic pattern layer 110. First imaging modality layer 120 creates a distinct image when used with radiographic imaging devices such as X-rays, CT and fluoroscopy devices. In some embodiments, first imaging modality layer may include a radiopaque ink disposed on the lower surface of graphic pattern layer 110. In other embodiments, first imaging modality layer 120 may comprise a radiopaque paste. In some embodiments, a hard-coated antimicrobial film 125 is stacked under first imaging modality layer 120 to provide structural support.

A second imaging modality layer 140 is stacked underneath first imaging modality layer 120. In keeping with the invention, second imaging modality layer 140 comprises a medical gel, e.g., a ballistic gel, composed of between 75% and 95% oil (non-food grade) and between 25% and 5% gelatin. Such gel has a melting point of between about 190 degrees Fahrenheit and 300 degrees Fahrenheit. In some embodiments, the gel is water insoluble, has a specific gravity of about 0.91 and a Shore rating of between about 3 and about 22 on the Shore OO scale. In addition, in some embodiments, the gel has a density of between about 830.0000 kg/m$^3$ and 985.0000 kg/m$^3$. Suitable gels include those available from Humimic Medical of Greenville, South Carolina sold under model numbers Gel #1, Gel #2, Gel #3, Gel #4 and Gel #5. Second imaging modality layer 140 creates a distinct image when used in, MRI and CT scans. In some embodiments, second imaging modality layer 140 may be affixed to first imaging modality layer 120 by an adhesive layer 145 disposed between first imaging modality layer 120 and second imaging modality layer 140. Additional imaging modality layers may be included in multi-modal fiducial marker 100 to facilitate marker detection under other imaging modalities.

In still another embodiment, the second imaging modality layer 140 may be provided with radiopaque additives.

A first adhesive layer 130 is disposed between second imaging modality layer 140 and film 125. A second adhesive layer 160 is disposed adjacent to and stacked underneath the second imaging modality layer 140. The first and second adhesive layers may comprise, e.g. a medical grade acrylic adhesive. A skin interface layer 165 which comprises a medical grade adhesive tape or adhesive foam suitable for patient skin contact may be stacked underneath second adhesive layer 160.

In keeping with an embodiment of the invention, each layer of multi-modal fiducial marker 100 is generally square with rounded corners and of generally equal surface area. The inventors determined that the generally square shape of the marker layers facilitates detection of 3D orientation of the marker using a single camera or a camera system.

Figure 2:
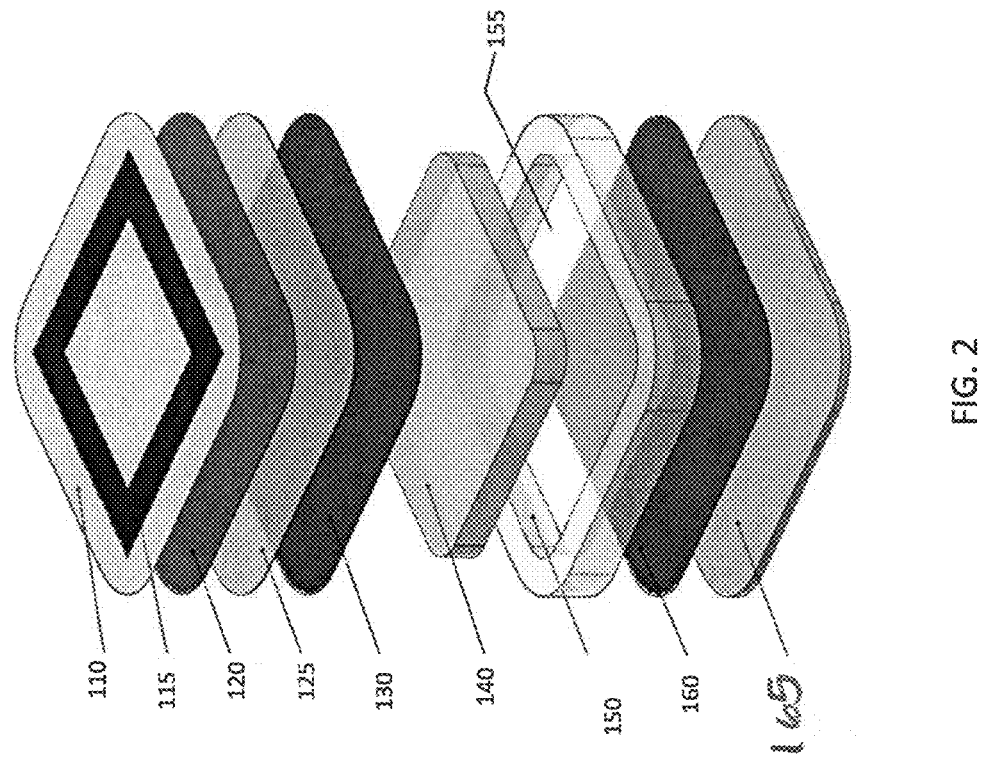
FIG. 2 illustrates an exploded view of a multi-modal marker in accordance with another embodiment of the invention.

In some embodiments, as illustrated in FIG. 2 for example, second imaging modality layer 140 is disposed in a cup 150 having a generally square trough 155 as illustrated in FIG. 2. Cup 150 is generally square with rounded corners. In this embodiment, second imaging modality layer 140 may comprise a solid square block.

Figure 3:
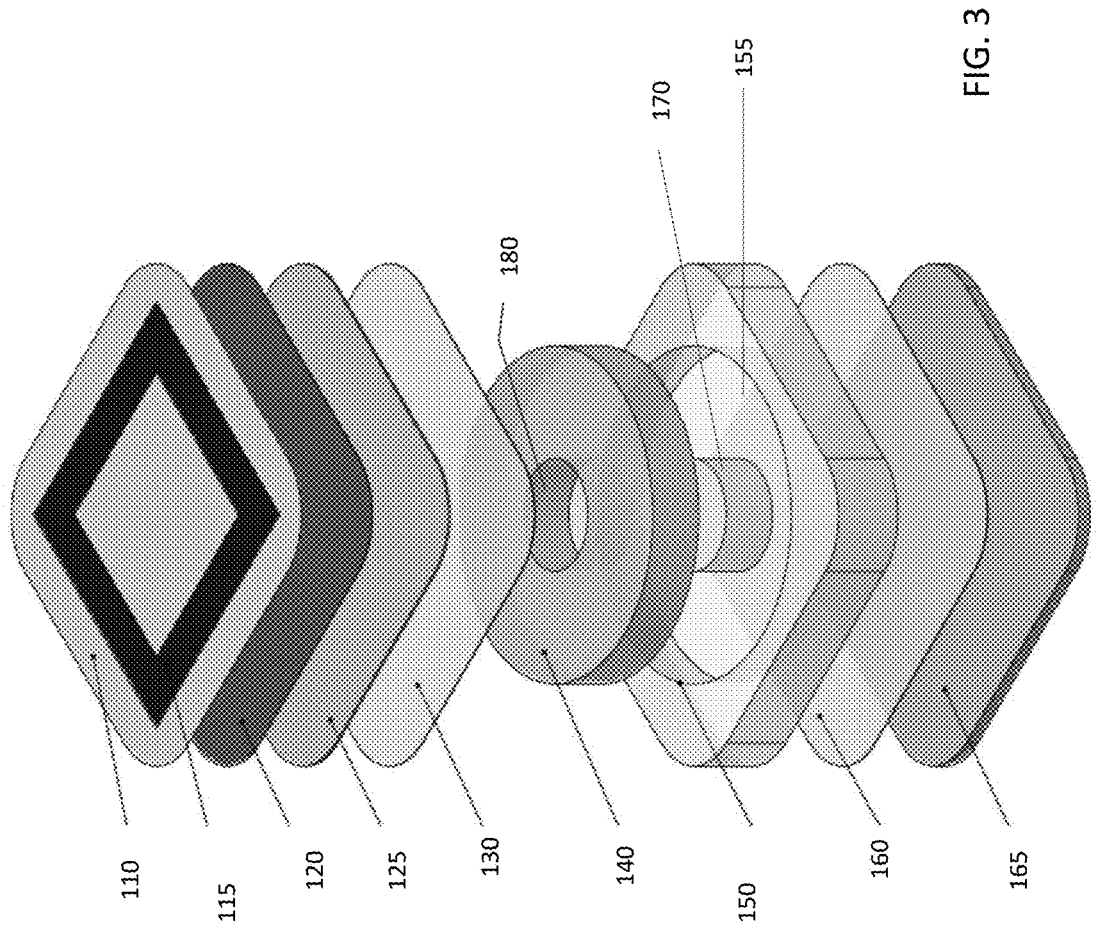
FIG. 3 shows an exploded view of a multi-modal marker in accordance with still another embodiment of the invention.

In other embodiments, second imaging modality layer 140 is disposed in a cup 150 having an annular trough 155 with a central post 170. See FIG. 3. In accordance with an aspect of the invention, second imaging modality layer 140 is annular and includes a central aperture 180 and is disposed in cup 150 such that central post 170 protrudes through central aperture 180. The presence of central aperture 180 facilitates precise detection of the center of marker 100 under MRI, by for example, providing an additional landmark on an image to help identify where MR/CT slices are cutting through the marker.

Figure 4:
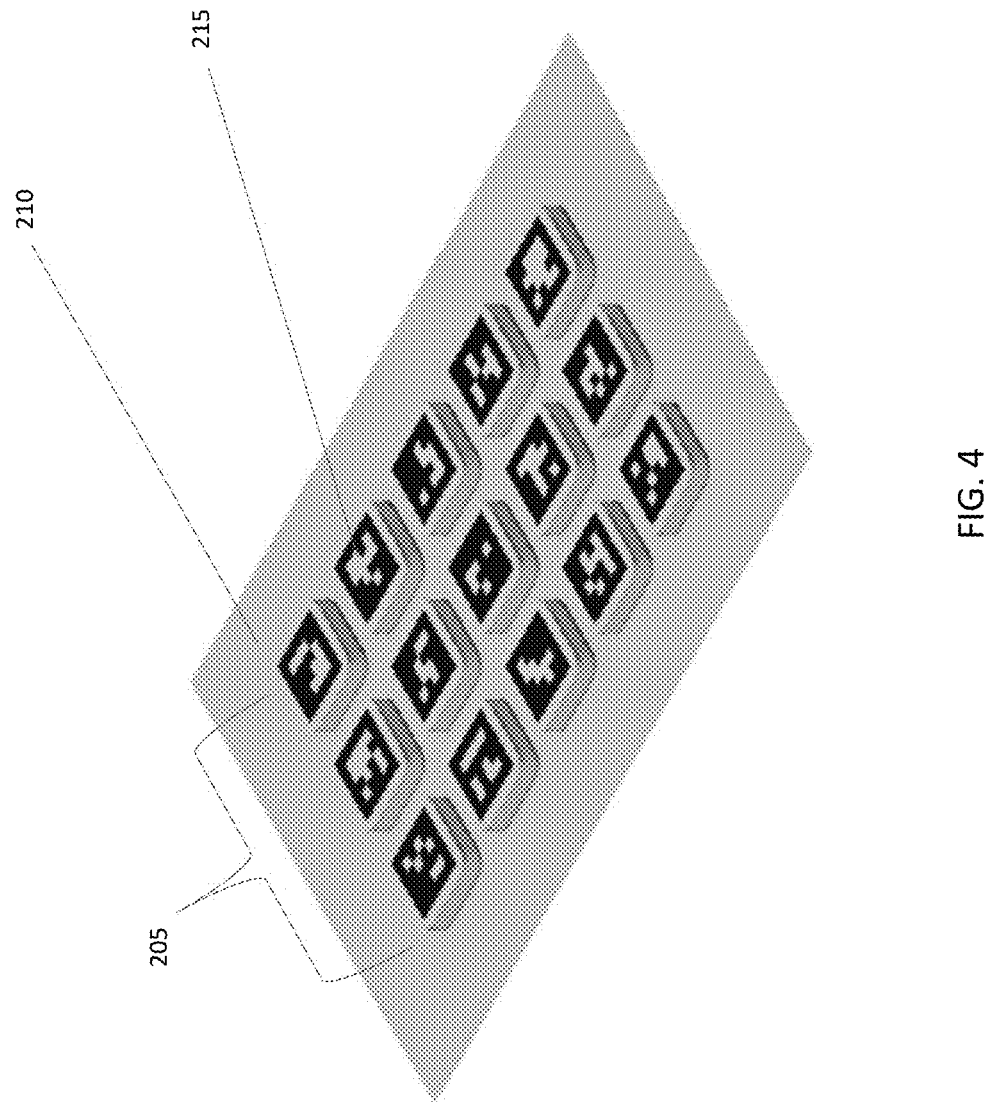
FIG. 4 depicts a set of multi-modal markers in accordance with an embodiment of the invention.

In some applications, it is advantageous to employ a set of multi-modal markers 205 constructed as described hereinabove, and each having a unique graphic pattern. During the initial registration of a constellation of markers, unique patterns allow each marker coming into camera view to be identified uniquely without confusing it with a previously seen marker. After registration, unique patterns help resolve 3D localization from as little as one marker. Accordingly, as illustrated in FIG. 4, in some embodiments a plurality of multi-modal markers 205 may be removably disposed on a liner 210. Each marker 205 includes a unique registration pattern 215. Suitable liners may be comprised of polyethylene foam with an acrylic adhesive.

Figure 5:
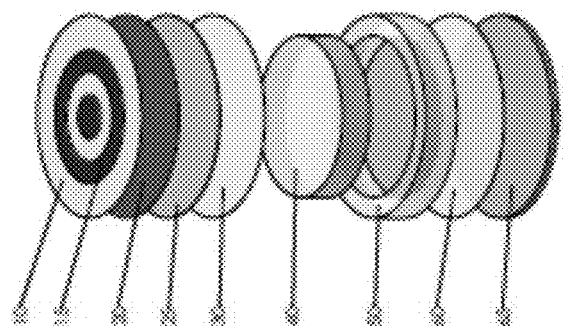
FIG. 5 depicts an exploded view of a multi-modal marker in accordance with a further embodiment of the invention.

While the marker disclosed herein has a generally square shape, the skilled artisan will recognize that the marker could take other shapes. For example, in keeping with the invention, the markers may take on a circular shape as depicted in FIG. 5.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the root terms "include" and/or "have", when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means plus function elements in the claims below are intended to include any structure, or material, for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

Although the present invention has been described in terms of particular example embodiments, it is not limited to those embodiments. The embodiments, examples, and modifications which would still be encompassed by the invention may be made by those skilled in the art, particularly in light of the foregoing teachings.

As used above "substantially," "generally," "about," and other words of degree are relative modifiers intended to indicate permissible variation from the characteristic so modified. It is not intended to be limited to the absolute value or characteristic which it modifies but rather possessing more of the physical or functional characteristic than its opposite, and preferably, approaching or approximating such a physical or functional characteristic.

Those skilled in the art will appreciate that various adaptations and modifications of the exemplary and alternative embodiments described above can be configured without departing from the scope and spirit of the invention. Therefore, it is to be understood that, within the scope of the appended claims, the invention may be practiced other than as specifically described herein.

The invention claimed is:

1. A multi-layer fiducial marker device comprising:
a first layer having an upper surface and a lower surface, the upper surface including a graphic pattern layer including dark pattern disposed on a white background, the lower surface being coated with a radiopaque material and a hard coat film layer disposed over the radiopaque material;
a cup having an upper rim, a trough and a lower surface;
a ballistic gel layer having an upper surface and a lower surface, the ballistic gel layer being disposed in the trough of said cup;

a first adhesive layer contiguous to the hard coat film layer, the upper surface of said ballistic gel layer and the rim of said cup; and
a second adhesive layer affixed to the lower surface of said cup,
wherein said first layer, said ballistic gel layer, said cup and said first and second adhesive layers are square with rounded corners.

2. The device of claim 1 wherein the dark pattern includes a dark square centered on the white background.

3. The device of claim 1 wherein said cup is acrylic.

4. The device of claim 1 wherein said ballistic gel layer has a density of between 830 kg/m$^3$ and 985 kg/m$^3$.

5. The device of claim 1 wherein said ballistic gel layer has Shore hardness of between about 3 and about 22 on the Shore 00 scale.

6. The device of claim 1 further comprising a skin interface layer disposed contiguous to said second adhesive layer.

7. A multi-layer fiducial marker device comprising:
a first layer having an upper surface and a lower surface, the upper surface including a dark pattern disposed on a white background, the lower surface being coated with a radiopaque material and a hard coat film layer disposed over the radiopaque material;
a first adhesive layer stacked underneath and contiguous to the lower surface of said first layer;
a cup having an upper rim, a trough and a lower surface, the trough being filled with a ballistic gel, said ballistic gel comprising between 75% and 95% non-food grade oil and between 25% and 5% gelatin, said cup being stacked underneath said first adhesive layer and the upper rim of said cup being contiguous to said first adhesive layer; and
a second adhesive layer affixed to the lower surface of the cup and stacked underneath said cup.

8. The multi-layer fiducial marker device of claim 7 wherein the lower surface of said cup covers an entire surface area of said second adhesive layer.

9. The device of claim 7 further comprising a skin interface layer stacked underneath and disposed contiguous to said second adhesive layer.

10. The device of claim 7 wherein said ballistic gel includes a central aperture.

11. The device of claim 10 wherein said cup includes a stem that protrudes upward from the lower surface of the cup through the central aperture.

12. The device of claim 11 wherein said ballistic gel is C-shaped.

13. The device of claim 11 wherein said ballistic gel is an annular disc.

14. The device of claim 10 wherein said cup is acrylic.

* * * * *